(12) United States Patent
Grubbs et al.

(10) Patent No.: US 8,846,939 B2
(45) Date of Patent: *Sep. 30, 2014

(54) IMIDAZOLIDINE-BASED METAL CARBENE METATHESIS CATALYSTS

(75) Inventors: Robert H. Grubbs, South Pasadena, CA (US); Matthias Scholl, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,708

(22) Filed: Jun. 12, 2012

(65) Prior Publication Data

US 2013/0165661 A1    Jun. 27, 2013

Related U.S. Application Data

(60) Continuation of application No. 12/016,482, filed on Jan. 18, 2008, now abandoned, which is a division of application No. 09/576,370, filed on May 22, 2000, now Pat. No. 7,329,758.

(60) Provisional application No. 60/142,853, filed on Jul. 7, 1999, provisional application No. 60/135,493, filed on May 24, 1999.

(51) Int. Cl.
*C07F 15/00* (2006.01)

(52) U.S. Cl.
CPC .................. *C07F 15/0046* (2013.01)
USPC ....................................................... 548/103

(58) Field of Classification Search
CPC ................................................. C07F 15/0046
USPC ......................................................... 548/103
See application file for complete search history.

(56) References Cited

U.S. PATENT DOCUMENTS

| | | | |
|---|---|---|---|
| 5,182,405 A | 1/1993 | Arduego, III | |
| 5,312,940 A | 5/1994 | Grubbs et al. | |
| 5,342,909 A | 8/1994 | Grubbs et al. | |
| 5,710,298 A | 1/1998 | Grubbs et al. | |
| 5,728,839 A | 3/1998 | Herrmann et al. | |
| 5,728,917 A | 3/1998 | Grubbs et al. | |
| 5,750,815 A | 5/1998 | Grubbs et al. | |
| 5,831,108 A | 11/1998 | Grubbs et al. | |
| 5,840,238 A | 11/1998 | Setiabudi et al. | |
| 5,936,100 A | 8/1999 | Furstner et al. | |
| 6,001,909 A | 12/1999 | Setiabudi | |
| 6,025,496 A | 2/2000 | Herrmann et al. | |
| 6,100,323 A | 8/2000 | Setiabudi et al. | |
| 6,635,768 B1 | 10/2003 | Herrmann et al. | |
| 7,329,758 B1 * | 2/2008 | Grubbs et al. | 548/103 |
| 7,378,828 B2 | 5/2008 | Brandt | |
| 7,622,590 B1 | 11/2009 | Nolan et al. | |
| 7,652,145 B2 | 1/2010 | Herrmann et al. | |
| 2011/0282068 A1 | 11/2011 | Herrmann et al. | |

FOREIGN PATENT DOCUMENTS

| | | |
|---|---|---|
| DE | 198 15 275 | 10/1999 |
| WO | WO 97/20865 | 6/1997 |
| WO | WO 97/29135 | 8/1997 |
| WO | WO 99/51344 | 10/1999 |
| WO | WO 00/15339 | 3/2000 |
| WO | WO 00/58322 | 10/2000 |

OTHER PUBLICATIONS

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," Org. Lett., vol. 1, No. 6, 1999, pp. 953-956.

Weskamp et al., "Highly Active Ruthenium Catalysts for Olefin Metathesis: The Synergy of N-Heterocyclic Carbenes and Coordinatively Labile Ligands," Angew. Chem., Int. Ed., vol. 38, No. 16, 1999, pp. 2416-2419.

Huang et al., "Olefin Metathesis-Active Ruthenium Complexes Bearing a Nucleophilie Carbene Ligand," J. Am. Chem. Soc. 1999, 121, pp. 2674-2678.

March, Advanced Organic Chemistry, 1985, 3rd Ed., Wiley, S. 17.

(Continued)

*Primary Examiner* — Joseph Kosack
(74) *Attorney, Agent, or Firm* — Nixon Peabody LLP; Jeffrey L. Costellia (57) ABSTRACT

The present invention relates to novel metathesis catalysts with an imidazolidine-based ligand and to methods for making and using the same. The inventive catalysts are

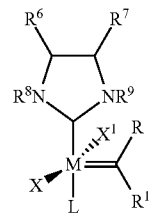

wherein:
M is ruthenium or osmium;
X and $X^1$ are each independently an anionic ligand;
L is a neutral electron donor ligand; and,
R, $R^1$ $R^6$, $R^7$, $R^8$, and $R^9$ are each independently hydrogen or a substituent selected for the group consisting of $C_1$-$C_{20}$ alkyl, $C_2$-$C_{20}$ alkenyl, $C_2$-$C_{20}$ alkynyl, aryl, $C_1$-$C_{20}$ alkoxycarbonyl, $C_1$-$C_{20}$ alkyithiol, aryl thiol, $C_1$-$C_{20}$ alkylsulfortyl and $C_1$-$C_{20}$ alkylsulfinyl, the substituent optionally substituted with one or more moieties selected from the group consisting of $C_1$-$C_{20}$ alkyl, $C_1$-$C_{10}$ alkoxy, aryl, and a functional group. The inclusion of an imidazolidine ligand to the previously described ruthenium or osmium catalysts has been found to dramatically improve the properties of these complexes.

13 Claims, 3 Drawing Sheets

(56) References Cited

OTHER PUBLICATIONS

Arduengo et al., "A Stable Diaminocarbene," J. Am. Chem. Soc. 1995, 117, pp. 11027-11028.
Arduengo et al., "Auf der Suche nach stabilen Carbenen," Chemie in unserer Zeit 1998, 32, pp. 6-14.
Lachmann et al., "Zur Kenntnis der anomalen α-Eliminicrung," Liebigs Ann. Chem. 1969, 729, pp. 27-32.
Wanzlick et al., "Nucleophile Carben-Chemie," Angew. Chem. 1961, 14, p. 493.
Enders et al., "Darstellung Struktur and Reaktivität von 1,3,4-Triphenyl-4,5-dihydro-1 H-1,2,4-triazol-5-yliden, einem neuen stabilen Carben," Angew. Chem. 1995, 107, pp. 1119-1122.
Dias et al., "Well-Defined Ruthenium Olefin Metathesis Catalysts: Mechanism and Activity," J. Am. Chem. Soc. 1997, 119, pp. 3887-3897.
Lappert, "The coordination chemistry of electron-rich alkenes (enetetramines)," J. Organomet. Chem. 1988, 358, pp. 185-214.
Hermann et al., "Nickel (II) Complexes of N-Heterocyclic Carbenes", Organometallics, 16, 2209-2212 (1997).
Hermann et al., "N-Heterocyclic Carbenes", Angew Chem. Int. Ed. Engl., 36, 2162-2187 (1997).
Glander et al., "Development and Application of Highly Efficient Ruthenium-Based Catalysts for the Ring Opening Metathesis Polymerization", Macromol. Symp. 127, 67-75 (1998).
Nolan, Steven P., "Synthetic Thermochemical and Catalytic Studies of Ruthenium and Rhodium Complexes", Jun. 26, 1998.
Hermann et al., "A Novel Class of Ruthenium Catalyst for Olefin Metathesis", Abstract: 11th International Symposium on Homogenous Catalysis, University of St. Andrews, Scotland U.K., Jul. 1998.
Weskamp, et al., "A Novel Class of a Novel Class of Ruthenium Catalyst for Olefin Metathesis", Angewandte Chemie International Edition, 37, 18, 2490-2493 (Oct. 2, 1998).
Ackermann et al., "Ruthenium Carbene Complexes with Imidazolin-2-ylidene Ligands Allow the Formation of Tetrasubstituted Cycloalkenes by RCM", Tetrahedron Letters, 40, 4787-4790 (1999).
Huang et al., "Influence of Sterically Demanding Carbene Ligation on Catalytic Behavior and Thermal Stability of Ruthenium Olefin Metathesis Catalysts", Organometallics, 18 5375-5380 (1999).
Weskamp, T. et al., "A Novel Class of Ruthenium Catalysts for Olefin Metathesis", Chemical Abstracts, Jan. 25, 1999, vol. 130, No. 4, p. 709, col. 2.
Scholl, M. et al., "Synthesis and Activity of a New Generation of Ruthenium-Based Olefin Metathesis Catalysts Coordinated with 1, 3-Dimesityl-4, 5-dihydroimidazol-2-ylidene Ligands", Chemical Abstracts, Nov. 22, 1999, vol. 131, No. 21, Abstract No. 285984k, col. 1.
Weskamp, T., "Highly Active Ruthenium Catalysts for Olefin Methatiesis: The Synergy of N-Heterocyclic Carbenes and Coordinatively Labile Ligands", Chemical Abstracts, Nov. 29, 1999, vol. 131, No. 22, p. 567, col. 1.

* cited by examiner

IMIDAZOLIDINE-BASED METAL CARBENE METATHESIS CATALYSTS

The present application claims the benefit of U.S. Provisional Application No. 60/135,493, filed May 24, 1999 by inventors Robert H. Grubbs and Matthias Scholl entitled SYNTHESIS OF RUTHENIUM-BASED OLEFIN METATHESIS CATALYSTS COORDINATED WITH 1,-3-DISUBSTITUTED-4,5-DIHYDRO-(4,5-DI-SUBSTITUTED)-IMEDAZOLE-2-YLIDENE LIGANDS and U.S. Provisional Application No. 60/142,853, filed Jul. 7, 1999 by inventors Robert H. Grubbs and Matthias Scholl entitled IMIDAZOLIDINE-BASED METAL CARBENE METATHESIS CATALYSTS which are incorporated herein by reference in their entireties.

The U.S. Government has certain rights in this invention pursuant to Grant No. GM31332 awarded by the National Institute of Health.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 which are all incorporated herein by reference. These publications describe well-defined single component ruthenium or osmium catalysts that possess several advantageous properties. For example, these catalysts are tolerant to a variety of functional groups and generally are more active than previously known metathesis catalysts. In an unexpected and surprising result, the inclusion of an imidazolidine ligand in these metal-carbene complexes has been found to dramatically improve the already advantageous properties of these catalysts. For example, the imidazolidine-based catalysts of the present invention exhibit increased activity and selectivity not only in ring closing metathesis ("RCM") reactions, but also in other metathesis reactions including cross metathesis ("CM") reactions, reactions of acyclic olefins, and ring opening metathesis polymerization ("ROMP") reactions.

SUMMARY

The present invention relates to novel metathesis catalysts with an imidazolidine-based ligand and to methods for making and using the same. The inventive catalysts are of the formula wherein:
M is ruthenium or osmium;
X and $X^1$ are each independently an anionic ligand;
L is a neutral electron donor ligand; and,
R, $R^1$ $R^6$, $R^7$, $R^8$, and $R^9$ are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, aryl thiol, $C_1$-$C_{20}$ alkylsulfonyl and $C_1$-$C_{20}$ alkylsulfinyl. Optionally, each of the R, $R^1$ $R^6$, $R^7$, $R^8$, and $R^9$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The inclusion of an imidazolidine ligand to the previously described ruthenium or osmium catalysts has been found to dramatically improve the properties of these complexes. Imidazolidine ligands are also referred to as 4,5-dihydro-imidazole-2-ylidene ligands. Because the imidazolidine-based complexes are extremely active, the amount of catalysts that is required is significantly reduced.

DETAILED DESCRIPTION OF THE PREFERRED EMBODIMENTS

The present invention generally relates to ruthenium and osmium carbene catalysts for use in olefin metathesis reactions. More particularly, the present invention relates to imidazolidine-based ruthenium and osmium carbene catalysts and to methods for making and using the same. The terms "catalyst" and "complex" herein are used interchangeably.

Unmodified ruthenium and osmium carbene complexes have been described in U.S. Pat. Nos. 5,312,940, 5,342,909, 5,728,917, 5,750,815, and 5,710,298, all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, aryl thiol, $C_1$-$C_{20}$ alkylsulfonyl and $C_1$-$C_{20}$ alkylsulfinyl. Optionally, each of the R or $R^1$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The catalysts of the present invention are as described above except that $L^1$ is an unsubstituted or substituted imidazolidine, resulting in a complex of the general formula wherein:

$R^6$, $R^7$, $R^8$, and $R^9$ are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxyl ate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, aryl thiol, $C_1$-$C_{20}$ alkylsulfonyl and $C_1$-$C_{20}$ alkylsulfinyl. Imidazolidine ligands are also referred to as 4,5-dihydro-imidazole-2-ylidene ligands.

In preferred embodiments of the inventive catalysts, the R substituent is hydrogen and the $R^1$ substituent is selected from the group consisting of $C_1$-$C_{20}$ alkyl, $C_2$-$C_{20}$ alkenyl, and aryl. In even more preferred embodiments, the $R^1$ substituent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —C═C(CH$_3$)$_2$.

In preferred embodiments of the inventive catalysts, L is selected from the group consisting of phosphine, sulfonated phosphine, phosphite, phosphinite, phosphorite, arsine, stibine, ether, amine, amide, imine, sulfoxide, carboxyl, nitrosyl, pyridine, and thioether. In more preferred embodiments, L is a phosphine of the formula $PR^3R^4R^5$, where $R^3$, $R^4$, and $R^5$ are each independently aryl or $C_1$-$C_{10}$ alkyl, particularly primary alkyl, secondary alkyl or cycloalkyl. In the most preferred embodiments, L is each selected from the group consisting of —P(cyclohexyl)$_3$, —P(cyclopentyl)$_3$, —P(isopropyl)$_3$, and —P(phenyl)$_3$.

In preferred embodiments of the inventive catalysts, X and $X^1$ are each independently hydrogen, halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, carboxylate, arylsulfonate, $C_1$-$C_{20}$ alkylsulfonate, $C_1$-$C_{20}$ alkylthiol, aryl thiol, $C_1$-$C_{20}$ alkylsulfonyl, or $C_1$-$C_{20}$ alkylsulfonyl. Optionally, X and $X^1$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, X and $X^1$ are halide, benzoate, $C_1$-$C_5$ carboxylate, $C_1$-$C_5$ alkyl, phenoxy, $C_1$-$C_5$ alkoxy, $C_1$-$C_5$ alkylthiol, aryl thiol, aryl, and $C_1$-$C_5$ alkyl sulfonate. In even more preferred embodiments, X and $X^1$ are each halide, $CF_3CO_2$, $CH_3CO_2$, $CFH_2CO_2$, $(CH_3)_3CO_3$ $(CF_3)_2(CH_3)CO$, $(CF_3XCH_3)_2CO$, PhO, MeO, EtO, tosylate, mesylate, or trifluoromethanesulfonate. In the most preferred embodiments, X and $X^1$ are each chloride.

In preferred embodiments of the inventive catalysts, $R^6$ and $R^7$ are each independently hydrogen, phenyl, or together form a cycloalkyl or an aryl optionally substituted with one or more moieties selected from the group consisting of $C_1$-$C_{10}$ alkyl, $C_1$-$C_{10}$ alkoxy, aryl, and a functional group selected from the group consisting of hydroxyl, thiol, thioether, ketone, aldehyde, ester, ether, amine, imine, amid; nitro, carboxylic acid, disulfide, carbonate, isocyanate, carbodiimide, carboalkoxy, carbamate, and halogen; and $R^8$ and $R^9$ are each is independently $C_1$-$C_{10}$ alkyl or aryl optionally substituted with $C_1$-$C_5$ alkyl, $C_1$-$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In more preferred embodiments, $R^6$ and $R^7$ are both hydrogen or phenyl, or $R^6$ and $R^7$ together form a cycloalkyl group; and $R^9$ and $R^9$ are each either substituted or unsubstituted aryl. Without being bound by theory, it is believed that bulkier $R^8$ and $R^9$ groups result in catalysts with improved characteristics such as thermal stability. In especially preferred embodiments, $R^8$ and $R^9$ are the same and each is independently of the formula wherein:

$R^{10}$, $R^{11}$, and $R^{12}$ are each independently hydrogen, $C_1$-$C_{10}$ alkyl, $C_1$-$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, $R^{10}$, $R^{11}$, and $R^{12}$ are each independently selected from the group consisting of hydrogen, methyl, ethyl, propyl, isopropyl, hydroxyl, and halogen. In the most preferred embodiments, $R^{10}$, $R^{11}$, and $R^{12}$ are the same and are each methyl.

Examples of the most preferred embodiments of the present invention include:

1

2

3

4

5

6 wherein Mes is (also known as "mesityl"); i-Pr is isopropyl; and $PCy_3$ is —P(cyclohexyl)$_3$.

Synthesis

In general, the catalysts of the present invention are made by contacting an imidazolidine with a previously described ruthenium/osmium catalyst whereby the imidazolidine replaces one of the L ligands. The imidazolidine may be made using any suitable method.

In preferred embodiments, the method for making the inventive catalysts comprises contacting an imidazolidine of the general formula with wherein:
M is ruthenium or osmium;
X and $X^1$ are each independently an anionic ligand;
L is a neutral electron donor ligand;
R, $R^1$ $R^6$, $R^7$, $R^8$, and $R^9$ are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, aryl thiol, $C_1$-$C_{20}$ alkylsulfonyl and $C_1$-$C_{20}$ alkylsulfinyl, the substituent optionally substituted with one or more moieties selected from the group consisting of $C_1$-$C_{10}$ alkyl, $C_1$-$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and,

$R^{13}$ is $C_1$-$C_{20}$ alkyl or aryl.

If desired, the contacting step may be performed in the presence of heat. Typically, the replacement reaction whereby the imidazolidine displaces one of the L ligands occurs in about 10 minutes in the presence of heat.

The imidazolidine may be synthesized by contacting a diamine with a salt to form an imidazolium salt; and then contacting the imidazolium salt with a base (preferably an alkyloxide) to make the imidazolidine in a form suitable for reacting with One embodiment for the synthetic method is as follows. First, a diketone is contacted with a Primary amine (R—$NH_2$ wherein $R^8$=$R^9$) or amines ($R^8$—$NH_2$ and $R^9$—$NH_2$) to form a diimine which is then reduced to form a diamine.

In preferred embodiments, $R^8$ and $R^9$ are the same and are each independently $C_1$-$C_{10}$ alkyl or aryl optionally substituted with $C_1$-$C_5$ alkyl, $C_1$-$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

When $R^6$ and $R^7$ together form a cycloalkyl and $R^8$ and $R^9$ are the same, the following alternate protocol may be used to make the diamine intermediate of the present invention:

wherein R' represents both $R^8$ and $R^9$ since $R^8$=$R^9$. Because a number of optically active primary cycloalkyldiamines are commercially available, this protocol may be used to synthesize optically active imidazolidine ligands. In addition, chiral metathesis complexes are also possible.

The diamine intermediate is used to prepare an imidazolium salt. In one embodiment, ammonium tetrafluoroborate may be used.

The resulting imidazolium salt is then reacted with a base to make the imidazolidine.

Representative examples of suitable bases include the r-BuOK/THF and MeONa/MeOH.

Metathesis Reactions

The catalysts of the present invention may be used for any metathesis reaction (i.e. ring opening metathesis polymerization, ring closing metathesis, cross metathesis, etc.) by contacting the inventive catalysts with an appropriate olefin. Any olefin may be used and as used herein an olefin is a substituted or unsubstituted alkene and is any compound including cyclic compounds that possess a carbon-carbon double bond. Unlike previously described metathesis catalysts, the inventive complexes can initiate reactions involving even highly substituted olefins such as tri and tetra substituted olefins (e.g., $R^1R^2C$=$CR^3R^4$ wherein $R^1$, $R^2$, $R^3$, and $R^4$ are independently each a hydrogen or a non-hydrogen moiety) and olefins bearing electron withdrawing groups.

In general, the method for performing a metathesis reaction comprises contacting a suitable olefin with a catalyst of the present invention. To date, the most widely used catalysts for ROMP and other metathesis reactions are

7

$$\text{Cl}_{\text{u...}}\underset{\underset{PCy_3}{|}}{\overset{\overset{PCy_3}{|}}{Ru}}=\!\!\!\!\!\!\!\!\!\!\!\!\!\!\!\!\!\!\!\!\!\!\!\!\!\!\!\!\!\!\!\!\!\!\!\!\!\!\!\!\!\text{Ph}$$

and

8

$$(F_3C)_2(H_3C)CO_{\text{...}}\underset{\underset{(F_3C)_2(H_3C)CO}{}}{\overset{\overset{Ar}{||}}{Mo}}=\!\!\!\!\!\!\!\!\!\!\!\!\!\!\!\!\text{Ph}$$

wherein $PCy_3$ is —P(cyclohexyl)$_3$ and Ar is $C_6H_3$-2,6-(PR). The molybdenum catalyst 8 displays much higher activity than the ruthenium catalyst 7, thus permitting polymerization of many sterically hindered or electronically deactivated cyclic olefins. However, the ruthenium catalyst 7 is stable under ambient conditions and tolerates a much larger range of protic and polar functional groups such as alcohols, acids and aldehydes. The catalysts of the present invention combine the best features of both complexes 7 and 8. In particular, the inventive imidazolidine catalysts rival and often exceed the activity of molybdenum complex 8 while maintaining the stability and functional group compatibility of ruthenium complex 7.

The enhanced properties of the inventive catalysts are illustrated by a series of experiments. For example, Table 1 contains representative results comparing the activities of two representative catalysts (1 and 2) of the present invention with complex 7 in several ring closing metathesis reactions with an acyclic olefin.

demanding olefins. For example, 2-tert-butyl-diethyl diallyl malonate ester (entry 3) can be cyclized with 5 mol % of catalyst 1 in one hour, with 5 mol % of catalyst 2 in twelve hours, while the corresponding reaction with 5 mol % of catalyst 7 does not yield any significant amount of cyclized

TABLE 1

Results of the RCM with 5 mol % cat. in 0.05M $CH_2Cl_2$ at reflux

| Entry | Substrate | Product | % Yield (Time, min) with catalyst 7 | % Yield (Time, min) with catalyst 1 | % Yield (Time, min) with catalyst 2[a] |
|---|---|---|---|---|---|
| 1 | (diethyl diallylmalonate) | (cyclopentene diester) | 100 (<30) | 100 (5) | 100 (8) |
| 2 | (methylated substrate) | (methylated cyclopentene) | 25 (12) 82 (30) | 100 (8) | 100 (12) |
| 3 | (t-Bu substrate) | (t-Bu cyclopentene) | N.R. (60) | 100 (60) | 65 (20) 92 (12 hrs) |
| 4 | (dimethyl substrate) | (tetrasubstituted cyclopentene) | N.R. (90) | N.R. | 14 (100) 47 (36 hrs) |
| 5 | (dimethyl hexenyl substrate) | (tetrasubstituted cyclohexene) | N.R. (90) | 90 (90) | 80 (60) 92 (12 hrs) |
| 6 | (diallyl polyether) | (crown ether product) | 39[b] (60) | 35[c] (60) | 55[c] (60) |

$E = CO_2Et$; [a] in $CD_2Cl_2$, conversion determined by 1H NMR, [b] E:Z = 1.6:1, [c] E:Z = 2.0:1

As it can be seen, the ring closure of diethyl diallylmalonate ester (entry 1) is completed in less than 10 minutes at 40° C. with both complexes 1 and 2 while complex 7 requires about 30 minutes. The increased activity of complexes 1 and 2 is most apparent in RCM reactions with more sterically product. Similarly, tetrasubstituted olefins (entries 4 and 5) can be prepared in moderate to excellent yields using complexes 1 and 2.

Table 2 shows the results of the same RCM experiments for previously described metathesis catalysts including complexes 7 and 8.

TABLE 2

RCM ACTIVITY COMPARISONS

| Substrate<br>E = CO$_2$Et | Product | 5 mol %, 0.10M C$_6$D$_6$, 65° C. | 5 mol %, 0.05M CD$_2$Cl$_2$, 40° C. |
|---|---|---|---|
|  |  | — | 30 min<br>100% |
|  |  | 24 hrs<br>100% | 30 min<br>82% |
|  |  | 24 hrs<br>96% | no reaction |
|  |  | 24 hrs<br>96% | no reaction |
|  |  | 24 hrs<br>61% | no reaction |
|  |  | — | 60 min<br>39%<br>E:Z = 1.6:1 |

TABLE 2-continued

RCM ACTIVITY COMPARISONS

| Substrate<br>E = CO$_2$Et | Product | 5 mol %, 0.05M CD$_2$Cl$_2$, 40° C. | 5 mol %, 0.05M CD$_2$Cl$_2$, 40° C. |
|---|---|---|---|
| | | 30 min<br>100% | 30 min<br>100% |
| | | 30 min<br>100% | — |
| | | 60 min<br>100% | 30 min<br>85% |
| | | 90 min<br>40% | 30 min<br>53% |
| | | 90 min<br>95% | 30 min<br>62% |
| | | 60 min<br>55%<br>E:Z = 2.0:1 | 30 min<br>73%<br>E:Z = 2.3:1 |

Since complexes 1 and 2 are much more reactive than complex 7, the use of lower catalysts loading for RCM reactions was investigated. The ring closure of diethyl diallylmalonate under the reaction conditions listed in Table 1 was conducted using 0.1, 0.05, and 0.01 mol % of catalysts (1 or 2) with respect to the substrate. In the first case, quantitative conversions within one hour were observed with both catalysts; in the second case, the conversion were quantitative with 1 (one hour) and 94% with 2 (three hours). In the third case, the conversions were nearly zero, which indicates that 0.01 mol % is at the lower limit of the catalyst loading for this type of RCM reactions.

The catalysts of the present invention are also useful for ROMP reactions. In general, the method involves contacting the catalyst with a cyclic olefin. The cyclic olefin substrate may be a single cyclic olefin or a combination of cyclic olefins (i.e. a mixture of two or more different cyclic olefins). The cyclic olefins may be strained or unstained, monocyclic or polycyclic, and may optionally include hetero atoms and/or one or more functional groups. Suitable cyclic olefins include but are not limited to norbornene, norbornadiene, dicyclopentadiene, cyclopentene, cycloheptene, cyclooctene, cyclooctadiene, cyclododecene, 7-oxanorbornene, 7-oxanorbomadiene, and derivatives therefrom. Illustrative examples of suitable functional groups include but are not limited to hydroxyl, thiol, ketone, aldehyde, ester, ether, amine, imine, amide, nitro, carboxylic acid, disulfide, carbonate, isocyanate, carbodiimide, carboalkoxy, and halogen. Preferred cyclic olefins include norbornene and dicyclopentadiene and their respective homologs and derivatives. The most preferred cyclic olefin is dicyclopentadiene ("DCPD").

The ROMP reaction may occur either in the presence or absence of solvent and may optionally include formulation auxiliaries. Known auxiliaries include antistatics, antioxidants, light stabilizers, plasticizers, dyes, pigments, fillers, reinforcing fibers, lubricants, adhesion promoters, viscosity-increasing agents and demolding enhancers. Illustrative examples of fillers for improving the optical physical, mechanical and electrical properties include glass and quartz in the form of powders, beads and fibers, metal and semimetal oxides, carbonates (i.e. $MgCO_3$, $CaCO_3$), dolomite, metal sulfates (such as gypsum and barite), natural and synthetic silicates (i.e. zeolites, wollastonite, feldspars), carbon fibers, and plastics fibers or powders.

The inventive catalysts' utility in ROMP reactions was demonstrated with polymerizations both endo- and exo-DCPD. Exposure of neat DCPD to catalyst 1 (10,000:1) yielded within seconds a hard, highly-crosslinked material. In fact, catalyst loadings as low as 130,000:1 have been used to make high-quality poly-DCPD product. In contrast, previously described ruthenium and osmium catalysts such as 7, required loadings of 7,000:1 to obtain similar poly-DCPD product.

As demonstrated by the synthesis of telechelic polybutadiene by chain transfer ROMP, the inventive catalysts are also extremely active in the polymerization of unstained cyclic olefins. For example, with a catalyst loading of about 12,000:1 (monomer to catalyst 1), the yield of telechelic polymers is higher (65%) than that using the bis-phosphine complex 7 at much lower monomer to catalyst ratio of 2,000:1 (50%).

High activities were also observed in the crossmetathesis of acyclic olefins. As an example, the cross metathesis of 9-decen-1-yl benzoate with cis-2-buten-1,4-diol diacetate catalyzed by 2 gave a high yield (80%) and a higher amount of the trans isomer (E:Z =9:1) compared to that when the corresponding bis-phosphine complex 7 was used (E:Z =4.7:1).

EXAMPLE 1

A synthetic protocol for a representative example of an imidazolidine ligand is as follows. Other imidazolidine ligands are made analogously.
Preparation of 1,2-dimesityl ethylene diimine:
A 300 mL round bottom flask was charged with acetone (50 mL), water (100 mL) and mesityl amine (10.0 g, 74 mmol). The solution was cooled to 0° C. and a solution of 40% glyoxal in water (5.38 g, 37 mmol) was added slowly. The reaction mixture was allowed to warm up to room temperature slowly and was stirred for additional 8 hours. The yellow precipitate formed was filtered off, briefly washed with cold acetone and air-dried to yield 1,2-dimesityl ethylene diimine.
Preparation of 1,2-dimesityl ethylene diamine:
(a) with $H_2$, Pd/C: A 50 mL round bottom flask was charged with 1,2-dimesityl ethylene diimine (300 mg, 1.01 mmol) and ethanol (20 mL). 10% Pd/C (30 mg) was added and a hydrogen balloon was attached via a needle. TLC indicated complete spot-to-spot conversion within 4 hours. The Pd catalyst was filtered off and the volatiles were pumped off in vacua to yield 1,2-dimesityl ethylene diamine.
(b) with $NaCNBH_3$: A 300 mL round bottom flask was charged with 1,2-dimesityl ethylene diimine (3.8 g, 13 mmol), methanol (100 mL) and $NaCNBH_3$ (4,92 g, 78 mmol). Concentrated HCl was added dropwise to maintain the pH below 4, and the reaction was stirred at room temperature for 20 hours (overnight). The solution was then diluted with 50 mL water, made basic with NaOH, and extracted thoroughly with $CH_2O_2$. The organic layer war dried over $MgSO_4$, filtered and the solvent was removed in vacuo to yield 1,2-dimesityl ethylene diamine (95% yield).
Preparation of 1,3-dimesityl-4,5-dihydro-imidazolium tetrafluoroborate:
Around bottom flask was charged with 1,2-dimesityl ethylene diamine (3.8 g, 12.8 mmol), triethyl orthoformate (15 mL) and ammonium tetrafluoroborate (1.35 g, 12.8 mmol). The reaction mixture was stirred at 120° C. for 4 hours at which time TLC indicated complete conversion. Volatiles were removed in vacuo and the product was used as prepared or it could be purified further by recrystallization from ethanol/hexanes.

EXAMPLE 2

Synthesis of $Cl_2Ru(=CHPh)(PCy_3)$(1.3-dimesityl-4,5-dihydro-2-imidazole):-imidazole
The imidazolidine ligand synthesized as detailed in Example 1 is used to prepare the corresponding imidazolidine catalyst ("complex 1") of the present invention. A 100-mL flame dried Schlenk flask equipped with a magnetic stir bar was charged with 1,3-dimesityl-4,5-dihydro-imidazolium tetrafluoroborate (394 mg, 1.0 mmol, 1 equiv.) and dry THF (20 mL) under nitrogen atmosphere. To this suspension, potassium tert-butoxide (122 mg, 1.0 mmol, 1 equiv.) was slowly added at room temperature. The tetrafluoroborate salt was dissolved immediately to give a yellow solution. The reaction mixture was allowed to stir at room temperature for one hour, followed by cannula transferring the reaction solution into another 100-mL dry Schlenk flask under Argon. The solvent was evaporated under high vacuum, followed by adding dry benzene (25 mL) and $RuCl_2(=CHPh)(PCy_3)_2$ (700 mg, 0.85 mmol, 0.85 equiv.). The reaction mixture was heated at 80° C. for 90 minutes. When the reaction was complete indicated by NMR, the volatiles were removed under high vacuum and the residue was washed by dry methanol (20 ml×4) to give pinkish brown microcrystalline solid (404 mg) in 56% yield: $^1H$ NMR ($CD_2Cl_2$, 400 MHz) δ 19.16 (s, 1H), 7.37-7.05 (m, 9H), 3.88 (s, 4H), 2.56-0.15 (m, 51H); $^{31}P$ NMR ($CD_2Cl_2$, 161.9 MHz) δ 31.41; HRMS (FAB) $C_{45}H_{65}Cl_2N_2PRu$ [M$^+$] 848.3306, found 848.3286.

EXAMPLE 3

Synthesis of Complex 2
A second example of synthetic protocol for making the inventive catalysts (complex 2) follows. 1,3-dimesityl-trans-hexahydrobenzoimidazolium tetrafluoroborate (272 mg, 0.61 mmol, 1.0 equiv.) was suspended in anhydrous tetrahydrofuran ("THF"; 5 mL) under inert atmosphere. To this suspension, potassium tert-butoxide ("KO$^t$Bu") was added (65 mg, 0.61 mmol, 1.0 equiv.). Immediately upon addition of KO$^t$Bu, the tetrafluoroborate salt dissolved completely and the reaction mixture turned yellow. Complex 7, RuCl$_2$(=CHPh)(PCy$_3$)$_2$ (400 mg, 0.49 mmol), was added to the reaction mixture as a solution in anhydrous benzene (15 mL). The reaction mixture was heated in an oil bath at 80° C. for 80 minutes at which time $^1$H NMR spectrum indicated a ratio of product (complex 2) to complex 7 of 95:5. Volatiles were removed in vacuo and the residue was washed under inert atmosphere with anhydrous pentane (4×20 mL) to give pure product as a pinkish-brown microcrystalline solid (270 mg, 0.3 mmol) in 61% yield. Scheme 1 illustrates this protocol for complex 2 as well as for complexes 1 and 3.

equiv.) and cis-2-buten-1,4-diol diacetate (160 µL, 1.014 mmol, 1.93 equiv.) in methylene chloride (2.5 mL, 0.21 M). After refluxing for 3.5 hours, the mixture was purified by flash column chromatography to yield the cross metathesis product as a clear, colorless oil (140 mg, 80% yield, E:Z=9:1).

ROMP Reactions with DCPD:

Complex 1 (6.5 mg, 7.5 µmol, 1 equiv.) in a small amount of CH$_2$Cl$_2$ (100 µL) was added to a stirring neat dicyclopentadiene (mixture of exo- and endo-isomers) (10.0 g, 75.6 mmol, 10,000 equiv.). Within a few seconds, the reaction mixture became increasingly viscous, warmed up significantly, and solidified shortly thereafter. On cooling, an odor free, nearly colorless solid was obtained.

Telechelic Synthesis:

Complex 1 (3.1 mg, 3.7 µmol, 1 equiv.) was added to a stirring mixture of cyclooctadiene (5.00 g, 46.2 mmol, 12,500

SCHEME 1

EXAMPLE 4

The following are representative protocols for several common metathesis reactions.

RCM Reactions

Complex 1 (42 mg, 50 µmol, 0.05 equiv.) was added to a solution of diethyl diallymalonate (240 mg, 1 mmol, 1 equiv.) in methylene chloride (20 mL, 0.05 M). The reaction mixture was refluxed on an oil bath (45° C.) for 5 minutes at which time $^1$H NMR indicated 100% conversion to cyclopent-3-ene-1,1-dicarboxylic acid diethyl ester.

Cross Metathesis Reactions:

Complex 2 (11 mg, 12 µmol, 0.023 equiv.) was added to a mixture of 9-decen-1-yl benzoate (145 µL, 0.525 mmol, 1 equiv.) and 1,4-dichloro-cis-2-butene (1.16 g, 928 mmol, 2,500 equiv.). After 8 hours, the reaction mixture was diluted with methylene chloride (1 mL) and poured into an excess of methanol precipitating the dichloro-telechelic polybutadiene as a white solid (4.0 g, 65% yield).

Polymerization of 5,6-Dihydroxycyclooctene

In a nitrogen filled drybox, a small vial was charged with 2 mg catalyst (1 equiv.), 150 mg 5,6-dihydroxycyclooctene (1000 equiv.), and 0.25 mL of benzene. The vial was capped tightly, removed from the drybox, and submerged in a constant temperature oil bath set at 50 degrees. After 10 hours, a slightly yellow viscous oil formed. Upon the addition of tetrahydrofuran, a white gel separated and was found to be insoluble in all common organic solvents. Residual, unreacted monomer could be detected in the tetrahydrofuran layer by $^1$H NMR.

EXAMPLE 5

Figure 1:
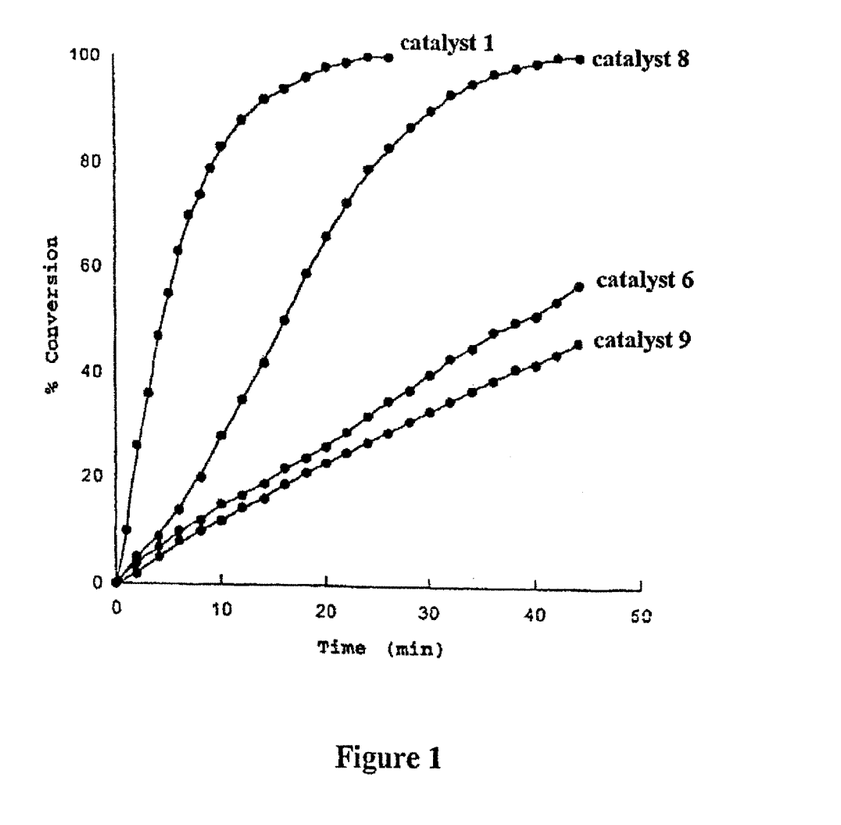
FIG. 1 compares the ROMP activity of COD of representative catalysts of the present invention with previously described metathesis catalysts as determined by $^1$H NMR spectroscopy. The reactions were performed at 20° C. with $CD_2Cl_2$ as solvent, a monomer/catalyst ratio of 300, and a catalyst concentration of 0.5 mM.
Figure 2:
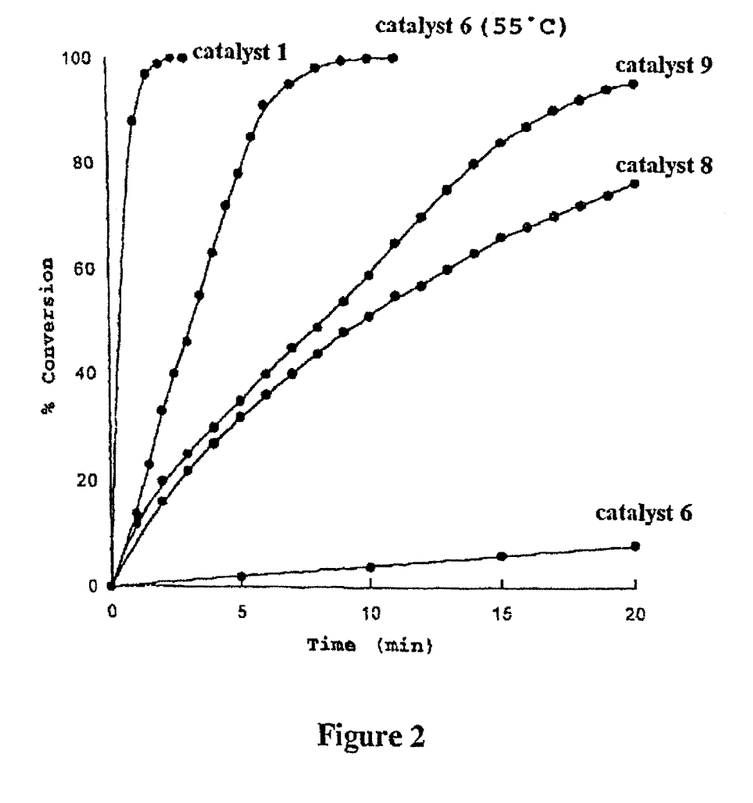
FIG. 2 compares the ROMP activity of COE of representative catalysts of the present invention with previously described metathesis catalysts as determined by $^1$H NMR spectroscopy. The reactions were performed at 20° C. with $CD_2Cl_2$ as solvent, a monomer/catalyst ratio of 300, and a catalyst concentration of 0.5 mM.
Figure 3:
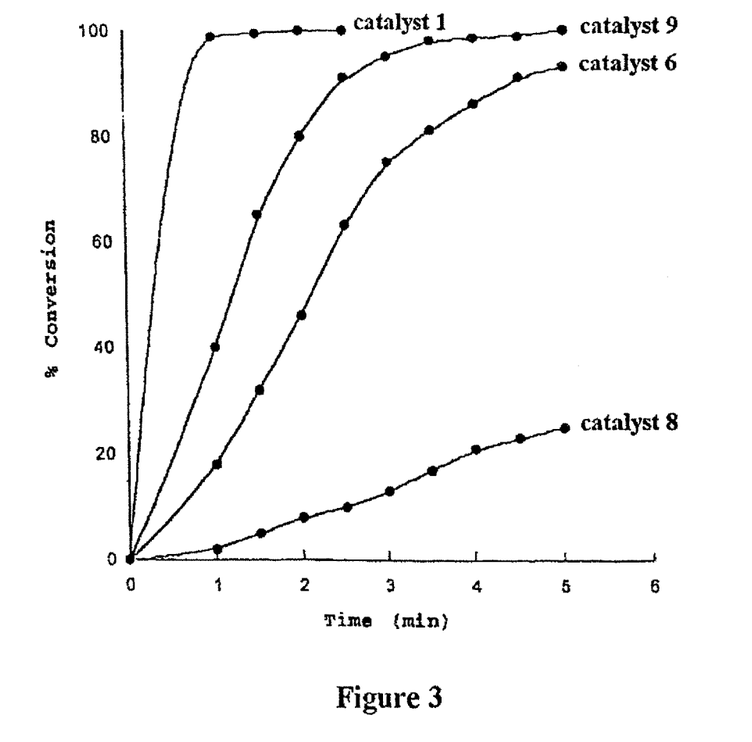
FIG. 3 compares the ROMP activity of COD at an elevated temperature of representative catalysts of the present invention with previously described metathesis catalysts as determined by $^1$H NMR spectroscopy. The reactions were performed at 55° C. with $CD_2Cl_2$ as solvent, a monomer/catalyst ratio of 300, and a catalyst concentration of 0.5 mM.

To better appreciate the advantageous properties of the inventive catalysts, the ROMP reactions of low strain cyclic olefins, cis, cis-cycloocta-1,5-diene ("COD") and cis-cyclooctene ("COE") with inventive catalysts 1 and 6 and representative prior art catalysts wherein Ar=C$_6$H$_3$-2,6-($^i$PR) ("catalyst 8") and wherein R=Mes ("catalyst 9") were compared. The molybdenum catalyst 8 was purchased from Strem Chemicals and recrystallized from pentane at −40° C. prior to use. For the ROMP kinetics experiments, COD, COE, and CD$_2$Cl$_2$ were distilled from CaH$_2$ and bubbled with argon prior to use. An polymerizations were performed under an atmosphere of nitrogen.

The ROMP of COD and COE were catalyzed with the respective catalysts and the percent monomer converted to polymer was followed over time using $^1$H NMR spectroscopy. As shown by FIGS. 1 and 2, the rate of polymerization at 20° C. using catalyst 1 was significantly higher than the molybdenum catalyst 8. As illustrated by FIG. 3, the rate of polymerization at 55° C. using catalysts 6 and 9 were also higher than for the molybdenum catalyst 8. Because the propagating species resulting from catalysts 1 and 6 are the same, the observed difference in polymerization rates between them is believed to be due to the initiation rate. The bulkier benzylidene is believed to facilitate phosphine dissociation thereby enhancing initiation to a greater extent than the dimenthylvinyl carbenc counterpart. Previous studies have shown that alkylidene electronics have a relatively small influence on the initiation rate.

Although imidazole-based catalysts such as catalyst 9 and the imidazoline-based catalyst of the present invention may appear structurally similar, they possess vastly different chemical properties due to the differences in their electronic character of the five membered ring. For example, the chemical differences between is as profound as the differences between

EXAMPLE 6

The catalysts of the present invention are capable of polymerizing a variety of low strain cyclic olefins including cyclooctadiene, cyclooctene, and several functionalized and sterically hindered derivatives with extremely low catalyst loadings (up to monomer/catalysts=100,000). Representative results are shown by Table 3.

TABLE 3

ROMP of various low strain cyclic olefins

| Monomer | Monomer to Catalyst Ratio | Temp. (° C.) | Time | Yield (%) | $M_n$ (PDI)$^a$ | % Trans$^b$ |
|---|---|---|---|---|---|---|
| 1,5 cyclooctadiene | 100,000 | 55 | 30 min | 85 | 112,400 (2.3) | 70 |
| | 10,000 | 25 | 24 h | 85 | 92,900 (2.5) | 85 |
| | 25,000 | 55 | 24 h | 89 | 10,700 (2.1) | 90 |
| cyclooctene | 100,000 | 55 | 5 min | e | e | f |
| | 10,000 | 25 | 30 min | e | e | f |
| | 25,000$^c$ | 55 | 24 h | 75 | 2200 (1.6) | 85 |

TABLE 3-continued

ROMP of various low strain cyclic olefins

| Monomer | Monomer to Catalyst Ratio | Temp. (° C.) | Time | Yield (%) | $M_n$ (PDI)[a] | % Trans[b] |
|---|---|---|---|---|---|---|
| 1-hydroxy 4-cyclooctene | 100,000 | 55 | 5 min | e | e | f |
|  | 10,000 | 25 | 30 min | e | e | f |
|  | 25,000[d] | 55 | 24 h | 85 | 2600 (2.3) | 85 |
| 1-acetoxy-4-cyclooctene | 10,000 | 55 | 5 min | 50 | 103,900 (2.8) | 85 |
|  | 1000 | 25 | 1 h | 60 | 79,300 (3.2) | 90 |
| 5-methylcyclopentene | 1000 | 25 | 24 h | 50 | 23,000 (2.5) | 50 |
| cyclopentene | 1000 | 25 | 24 h | 52 | 9000 (3.5) | 90 |

[a]Determined by $CH_2Cl_2$ or THF GPC and results are reported relative to poly(styrene) standards;
[b]Percent trans olefin in the polymer backbone as determined by 1H and 13C NMR analysis;
[c]1,4-diacetoxy-cis-2-butene was included as a chain transfer agent ("CTA") wherein the Monomer/CTA = 80;
[d]Monomer/CTA = 10, [Monomer]$_0$ = 4.5M in $C_2H_4Cl_2$;
[e]Polymer was insoluble;
[f]Not determined.

Elevated temperatures (55° C.) generally increased the yields of polymer while reducing reaction times. The inclusion of acyclic olefins which act as chain transfer agents controlled the molecular weights. The addition of CTAs is desirable when insoluble polymers are obtained by ring-opening monomers such as COE in bulk. Polymers possessing alcohols or acetic ester along their backbone could also be prepared using functionalized monomers such as 5-hydroxy- or 5-acetoxy-cyclooctene. The functional groups on these polymers could easily be derivatized to form graft copolymers or side-chain liquid crystalline polymers. In general, $^1$H NMR spectroscopy indicated a predominantly (70-90%) trans-olefin microstructure in these polymers. As expected for an equilibrium controlled polymerization where chain transfer occurs, longer polymerization times resulted in higher trans-olefin values.

EXAMPLE 7

A highly strained monomer, exo,exo-5,6-bis(methoxymethyl)-7-oxabicyclo[2.2.1]hept-2-ene, was polymerized via ROMP reaction using catalyst 1 in the presence of 1,4-diacetoxy-2-butene as a chain transfer agent. The reaction was conducted in $C_2H_4Cl_2$ at 55° C. for 24 hours and resulted in a bis-(acetoxy) end-terminated polymer in 80% yield (Mn=6300, PDI 2.0). This result is particularly notable since telechelic polymers composed of highly strained monomers are relatively difficult to obtain using other methods. For example, a metathesis degradation approach using a tungsten analog of catalyst 8 has been used to prepare telechelic poly(oxanorbornene)s and poly(norbornene)s. However, only certain telechelic polymers are amenable to this approach since the limited ability of the tungsten catalyst to tolerate functional groups imposes a severe restriction on the range of chain transfer agents that may be used. Alternatively, a "pulsed addition" approach has been used with catalysts 7 and 8. However, because monomer and/or CTA must be added in a carefully timed manner, this approach is relatively difficult to perform and is not readily amenable to industrial applications.

EXAMPLE 8

1,5-dimethyl-1,5-cyclooctadiene, a sterically hindered, low strain, di-substituted cyclic olefin was polymerized using catalyst 1. The 1,5-dimethyl-1,5-cyclooctadiene used in this study contained 1,6-dimethyl-1,5-cyclooctadiene (20%) as an inseparable mixture. This ROMP reaction was performed at 55° C. with monomer/catalyst ratio of 1000 and resulted in a 90% yield of poly(isoprene) having a $M_n$ of 10,000 and a PDI of 2.3. To the best of our knowledge, this example represents the first ROMP of this monomer. Subsequent hydrogenation using p-toluenesulfonhydrazide as a hydrogen source afforded an ethylene-propylene copolymer in quantitative yield (as determined by NMR analysis). Previously, a six step synthesis was necessary to obtain a similar copolymer via a metathetical route.

The resulting ethylene-propylene copolymer was not "perfectly" alternating because of the impurity in the 1,5-dimethyl-1-5-cyclooctadiene starting material. However, since trisubstituted alkylidenes were not observed as a side product, poly(isoprene) product having perfectly alternating head to tail microstructure would have likely been formed if a higher grade of 1,5-dimethyl-1-5-cyclooctadiene were used. As a result, practice of the present invention could result in a perfectly alternating ethylene-propylene product.

EXAMPLE 9

2-methyl-1-undecene (110 µL, 0.5 mmol) and 5-hexenyl-1-acetate (170 µL, 1.0 mmol) were simultaneously added via syringe to a stirring solution of complex 1 (20 mg, 0.024 mmol, 4.8 mol %) in $CH_2Cl_2$ (2.5 mL). The flask was fitted with a condenser and refluxed under nitrogen for 12 hours. The reaction mixture was then reduced in volume to 0.5 ml and purified directly on a silica gel column (2×10 cm), eluting with 9:1 hexane:ethyl acetate. A clear oil was obtained (83 mg, 60% yield, 2.3:1 trans/cis as determined by relative intensity of alkene $^{13}$C peaks at 125.0 and 124.2 ppm). $^1$H NMR (300 MHz, CDCl$_3$, ppm): 5.08 (1H, t, J=2.0 Hz), 4.04 (2H, t, J=6.0 Hz), 2.03 (3H, obs s), 2.01-1.91 (2H, m), 1.69-1.59 (2H, m), 1.56 (3H, obs s), 1.47-1.05 (16H, broad m), 1.05-0.84 (3H, t, J=6.8 Hz) $^{13}$C NMR (75 MHz, CDCl$_3$, ppm): 171.7, 136.7, 136.4, 125.0, 124.2, 123.3, 65.1, 40.3, 32.5, 32.3, 30.2, 29.9, 28.8, 28.6, 28.5, 28.0, 26.7, 232, 21.5, 16.4, 14.7. R$_f$=0.35 (9:1 hexane:ethyl acetate); HRMS (EI) calcd for $C_{18}H_{34}O_2$ [M]$^+$ 282,2559, found 282.2556.

EXAMPLE 10

9-Decen-1(tert-butyldimethylsilane)-yl (330 µL, 1.0 mmol) and Methyl methacrylate (55 µL, 0.51 mmol) were added simultaneously via syringe to a stirring solution of complex 1 (21 mg, 0.026 mmol, 5.2 mol %) in $CH_2Cl_2$ (2.5 ml). The flask was fitted with a condenser and refluxed under nitrogen for 12 hours. The reaction mixture was then reduced in volume to 0.5 ml and purified directly on a silica gel column (2×10 cm), eluting with 9:1 hexane:ethyl acetate. A viscous oil was obtained (110 mg, 62% yield, only trans isomer detected in $^1$H and $^{13}$C NMR spectra). $^1$H NMR (300 MHz, CdCl$_3$, ppm): δ 6.75 (1H, m), 3.71 (3H, s), 3.57 (2H, t, J=6.3 Hz), 2.14 (2H, m), 1.81 (3H, app s), 1.50-1.05 (12H, broad m), 0.87 (9H, s), 0.02 (6H, s). $^{13}$C NMR (75 MHz, CDCl$_3$, ppm): δ 169.2, 143.2, 128.0, 63.8, 52.1, 33.4, 30.0, 29.8, 29.2, 29.1, 26.5, 26.3, 18.9. 12.9. R$_f$=0.81 (9:1 hexane: ethyl acetate); HRMS (EI) calcd for C$_{19}$H$_{38}$O$_3$Si [M+H]$^+$ 343.2668, found 343.2677. Elemental analysis calcd; C: 66.61, H: 11.18; found: C; 66.47, H: 11.03.

What is claimed is:

1. A composition of matter comprising a compound having the formula:

where:
M is Ru or Os;
X and X$^1$ are each independently an anionic ligand;
P is phosphorus;
R$^g$, R$^h$ and R$^i$ are each independently:
  (1) a C$_{1-10}$ alkyl group,
  (2) a C$_{3-10}$ cycloalkyl group or
  (3) a C$_{5-20}$ aryl group;
R, R$^6$, R$^7$, R$^8$, and R$^9$ are each independently:
  (1) hydrogen,
  (2) a C$_{1-10}$ alkyl group,
  (3) a C$_{2-20}$ alkenyl group,
  (4) a C$_{2-20}$ alkynyl group,
  (5) an aryl group,
  (6) a C$_{1-20}$ carboxylate group,
  (7) a C$_{1-20}$ alkoxy group,
  (8) a C$_{2-20}$ alkenyloxy group,
  (9) a C$_{2-20}$ alkenyloxy group,
  (10) an aryloxy group,
  (11) a C$_{2-20}$ alkoxycarbonyl group,
  (12) a C$_{1-20}$ alkylthiol group,
  (13) a C$_{1-20}$ alkylsulfonyl group,
  (14) a C$_{1-20}$ alkylsulfinyl group,
where each of R, R$^6$, R$^7$, R$^8$, and R$^9$ is optionally substituted with
  (a) halogen,
  (b) a C$_{1-10}$ alkyl group,
  (c) a C$_{1-10}$ alkoxy group,
  (d) an aryl group
  (e) a hydroxyl group,
  (f) a thiol group,
  (g) a thioester group,
  (h) a ketone group,
  (i) an aldehyde group,
  (j) an ester group,
  (k) an ether group,
  (l) an amino group,
  (m) an amido group,
  (n) an imino group,
  (o) a nitro group,
  (p) a carboxylic acid group,
  (q) a disulfide group,
  (r) a carbonate group,
  (s) an isocyanate group,
  (t) a carbodiimide group,
  (u) a carboalkoxy group, or
  (v) a carbamate group.

2. An olefin metathesis catalyst wherein the metathesis catalyst has the following structure:

wherein,
M is ruthenium or osmium;
X and X$^1$ are each independently an anionic ligand;
L$^1$ is an imidazolidine ligand;
L is a neutral electron donor ligand; and
R and R$^1$ are each independently hydrogen, C$_{1-10}$ alkyl, C$_{2-20}$ alkenyl, C$_{2-20}$ alkynyl, aryl, C$_{1-20}$ carboxylate, C$_{1-20}$ alkoxy, C$_{2-20}$ alkenyloxy, C$_{2-20}$ alkynyloxy, aryloxy, C$_{2-20}$ alkoxycarbonyl, C$_{1-20}$ alkylthiol, aryl thiol, C$_{1-20}$ alkylsulfonyl, and C$_{1-20}$ alkylsulfinyl, and wherein each of R and R$^1$ is optionally substituted with halogen, C$_{1-10}$ alkyl, C$_{1-10}$ alkoxy, aryl, hydroxyl, thiol, thioether, ketone, aldehyde, ester, ether, amino, amido, imino, nitro, carboxylic acid, disulfide, carbonate, isocyanate, carbodiimide, carboalkoxy, or carbamate; and
wherein at least one of L, L$^1$, R, R$^1$, X, and X$^1$ may be linked with at least one of L, L$^1$, R, R$^1$, X, and X$^1$ to form a bonded ligand array or a bidentate ligand.

3. The metathesis catalyst of claim 2, wherein the imidazolidine ligand has the following structure:

wherein,
R$^6$, R$^7$, R$^8$, and R$^9$ are each independently hydrogen, C$_{1-10}$ alkyl, C$_{2-20}$ alkenyl, C$_{2-20}$ alkynyl, aryl, C$_{1-20}$ carboxylate, C$_{1-20}$ alkoxy, C$_{2-20}$ alkenyloxy, C$_{2-20}$ alkynyloxy, aryloxy, C$_{2-20}$alkoxycarbonyl, C$_{1-20}$ alkylthiol, aryl thiol, C$_{1-20}$ alkylsulfonyl, and C$_{1-20}$ alkylsulfinyl, and wherein each of R$^6$, R$^7$, R$^8$, and R$^9$ is optionally substituted with halogen, C$_{1-10}$ alkyl, C$_{1-10}$ alkoxy, aryl, hydroxyl, thiol, thioether, ketone, aldehyde, ester, ether, amino, amido, imino, nitro, carboxylic acid, disulfide, carbonate, isocyanate, carbodiimide, carboalkoxy, or carbamate.

4. The metathesis catalyst of claim 2, wherein at least one of L, L$^1$, R, R$^1$, X, and X$^1$ is linked with at least one of L, L$^1$, R, R$^1$, X, and X$^1$ to form a bonded ligand array.

5. The metathesis catalyst of claim 2, wherein L is bonded together with one of X and X$^1$ to form a bidentate ligand.

6. The metathesis catalyst of claim 2, wherein L is bonded together with one of R and $R^1$ to form a bidentate ligand.

7. The metathesis catalyst of claim 2, wherein R and $R^1$ are bonded together.

8. The metathesis catalyst of claim 2, wherein the metathesis catalyst has the following structure:

wherein,
M is ruthenium or osmium;
X and $X^1$ are each independently an anionic ligand;
L is a neutral electron donor ligand; and
R, $R^1$, $R^6$, $R^7$, $R^8$, and $R^9$ are each independently hydrogen, $C_{1-10}$ alkyl, $C_{2-20}$ alkenyl, $C_{2-20}$ alkynyl, aryl, $C_{1-20}$ carboxylate, $C_{1-20}$ alkoxy, $C_{2-20}$ alkenyloxy, $C_{2-20}$ alkynyloxy, aryloxy, $C_{2-20}$ alkoxycarbonyl, $C_{1-20}$ alkylthiol, aryl thiol, $C_{1-20}$ alkylsulfonyl, and $C_{1-20}$ alkylsulfinyl, and wherein each of R and $R^1$ is optionally substituted with halogen, $C_{1-10}$ alkyl, $C_{1-10}$ alkoxy, aryl, hydroxyl, thiol, thioether, ketone, aldehyde, ester, ether, amino, amido, imino, nitro, carboxylic acid, disulfide, carbonate, isocyanate, carbodiimide, carboalkoxy, or carbamate.

9. The metathesis catalyst of claim 8, wherein at least one of L, $L^1$, R, $R^1$, $R^8$, $R^9$, X, and $X^1$ is linked with at least one of L, $L^1$, R, $R^1$, $R^8$, $R^9$, X, and $X^1$ to form a bonded, bidentate, or multidentate ligand array.

10. The metathesis catalyst of claim 8, wherein L is bonded together with one of X and $X^1$ to form a bidentate ligand.

11. The metathesis catalyst of claim 8, wherein L is bonded together with one of R and $R^1$ to form a bidentate ligand.

12. The metathesis catalyst of claim 8, wherein R and $R^1$ are bonded together.

13. A metathesis catalyst wherein the metathesis catalyst has the following structure:

wherein,
M is Ru or Os;
X and $X^1$ are each independently an anionic ligand;
P is phosphorus;
$R^g$, $R^h$ and $R^i$ are each independently:
  (1) a $C_{1-10}$ alkyl group,
  (2) a $C_{3-10}$ cycloalkyl group or
  (3) a $C_{5-20}$ aryl group;
R, $R^6$, $R^7$, $R^8$, and $R^9$ are each independently:
  (1) hydrogen,
  (2) a $C_{1-10}$ alkyl group,
  (3) a $C_{2-20}$ alkenyl group,
  (4) a $C_{2-20}$ alkynyl group,
  (5) an aryl group,
  (6) a $C_{1-20}$ carboxylate group,
  (7) a $C_{1-20}$ alkoxy group,
  (8) a $C_{2-20}$ alkenyloxy group,
  (9) a $C_{2-20}$ alkynyloxy group,
  (10) an aryloxy group,
  (11) a $C_{2-20}$ alkoxycarbonyl group,
  (12) a $C_{1-20}$ alkylthiol group,
  (13) a $C_{1-20}$ alkylsulfonyl group,
  (14) a $C_{1-20}$ alkylsulfinyl group,
where each of R, $R^6$, $R^7$, $R^8$, and $R^9$ is optionally substituted with
  (a) halogen,
  (h) a $C_{1-10}$ alkyl group,
  (c) a $C_{1-10}$ alkoxy group,
  (d) an aryl group
  (e) a hydroxyl group,
  (f) a thiol group,
  (g) a thioester group,
  (h) a ketone group,
  (i) an aldehyde group,
  (j) an ester group,
  (k) an ether group,
  (l) an amino group,
  (m) an amido group,
  (n) an imino group,
  (o) a nitro group,
  (p) a carboxylic acid group,
  (q) a disulfide group,
  (r) a carbonate group,
  (s) an isocyanate group,
  (t) a carbodiimide group,
  (u) a carboalkoxy group, or
  (v) a carbamate group.

* * * * *